United States Patent [19]
Forman et al.

[11] Patent Number: 5,514,092
[45] Date of Patent: May 7, 1996

[54] DRUG DELIVERY AND DILATATION-DRUG DELIVERY CATHETERS IN A RAPID EXCHANGE CONFIGURATION

[75] Inventors: Michael R. Forman, St. Paul; Lori L. Stowell, Coon Rapids, both of Minn.

[73] Assignee: Schneider (USA) Inc., Plymouth, Minn.

[21] Appl. No.: 287,121

[22] Filed: Aug. 8, 1994

[51] Int. Cl.⁶ ................................................. A61M 29/00
[52] U.S. Cl. ........................... 604/101; 604/104; 606/194
[58] Field of Search ..................... 604/96–103, 265–266, 604/269, 280; 606/194

[56] References Cited

U.S. PATENT DOCUMENTS

| | | |
|---|---|---|
| 3,948,254 | 4/1976 | Zaffaroni . |
| 4,299,226 | 11/1981 | Banka . |
| 4,417,576 | 11/1983 | Baran . |
| 4,423,725 | 1/1984 | Baran et al. . |
| 4,445,892 | 5/1984 | Hussein et al. . |
| 4,464,176 | 8/1984 | Wijayarathna . |
| 4,531,936 | 7/1985 | Gordon . |
| 4,573,966 | 3/1986 | Weikl et al. . |
| 4,610,662 | 9/1986 | Weikl et al. . |
| 4,636,195 | 1/1987 | Wolinsky . |
| 4,655,746 | 4/1987 | Daniels et al. . |
| 4,708,718 | 11/1987 | Daniels . |
| 4,748,982 | 6/1988 | Horzewski et al. . |
| 4,762,129 | 8/1988 | Bonzel . |
| 4,799,479 | 1/1989 | Spears . |
| 4,824,436 | 4/1989 | Wolinsky . |
| 4,832,688 | 5/1989 | Sagae et al. . |
| 4,911,163 | 3/1990 | Fina . |
| 4,927,418 | 5/1990 | Dake et al. . |
| 4,968,306 | 11/1990 | Huss et al. . |
| 4,968,307 | 11/1990 | Dake et al. . |
| 4,983,166 | 1/1991 | Yamawaki . |
| 4,994,033 | 2/1991 | Shockey et al. . |
| 5,019,075 | 5/1991 | Spears et al. . |
| 5,021,044 | 6/1991 | Sharkawy . |
| 5,026,607 | 6/1991 | Klezulas . |
| 5,040,548 | 8/1991 | Yock . |
| 5,049,132 | 9/1991 | Shaffer et al. . |
| 5,061,273 | 10/1991 | Yock . |

(List continued on next page.)

FOREIGN PATENT DOCUMENTS

| | | |
|---|---|---|
| 0383429 | 1/1990 | European Pat. Off. . |
| 0526102A1 | 7/1992 | European Pat. Off. . |
| WO86/05990 | 10/1986 | WIPO . |
| 9002579 | 3/1990 | WIPO . |
| WO92/11896 | 7/1992 | WIPO . |
| WO92/11895 | 7/1992 | WIPO . |
| 9411053 | 5/1994 | WIPO . |
| 9414495 | 7/1994 | WIPO . |

OTHER PUBLICATIONS

Stephen R. Hanson, Ph.D., "Intralumenal Drug Delivery for Experimental Thrombosis and Restenosis," *Restenosis Summit V*, May 20, 1993, pp. 296–300.

Spencer B. King III, M.D., "Localized Endovascular Therapy for Interventional Cardiology," *Restenosis Summit V*, May 20, 1993, pp. 280–281.

Robert J. Levy, M.D., "Local Delivery:Polymer Methods," *Restenosis Summit V*, May 20, 1993, pp. 316–320.

*Primary Examiner*—C. Fred Rosenbaum
*Assistant Examiner*—Perry E. Van Over
*Attorney, Agent, or Firm*—Peter C. Richardson; Lawrence C. Akers; Philip C. Strassburger

[57] ABSTRACT

Catheters for drug delivery or for both dilatation and drug delivery are provided with a guide wire lumen terminating within the catheter shaft and having an opening through the catheter shaft to enable a guide wire to exit the catheter shaft substantially distal to the proximal end of the catheter. In one embodiment, drug delivery ports are provided between occlusion balloons. In another embodiment, a dilatation balloon is also provided between the occlusion balloons. In another embodiment, a double layered balloon is provided to simultaneously dilatate the stenosis and deliver medication to the site. Alternatively, a balloon can be provided which only delivers medication.

35 Claims, 8 Drawing Sheets

U.S. PATENT DOCUMENTS

| | | |
|---|---|---|
| 5,087,244 | 2/1992 | Wolinsky et al. . |
| 5,087,394 | 2/1992 | Keith . |
| 5,090,960 | 2/1992 | Don Michael . |
| 5,092,841 | 3/1992 | Spears . |
| 5,098,381 | 3/1992 | Schneider . |
| 5,102,402 | 4/1992 | Dror et al. . |
| 5,112,305 | 5/1992 | Barath et al. . |
| 5,135,484 | 8/1992 | Wright . |
| 5,135,516 | 8/1992 | Sahatjian et al. . |
| 5,163,905 | 11/1992 | Don Michael . |
| 5,176,638 | 1/1993 | Don Michael . |
| 5,180,366 | 1/1993 | Woods . |
| 5,199,951 | 4/1993 | Spears . |
| 5,209,730 | 5/1993 | Sullivan . |
| 5,213,576 | 5/1993 | Abiuso et al. . |
| 5,222,941 | 6/1993 | Don Michael . |
| 5,236,413 | 8/1993 | Feiring . |
| 5,236,424 | 8/1993 | Imran . |
| 5,242,397 | 9/1993 | Barath et al. . |
| 5,267,959 | 12/1993 | Forman . |
| 5,272,012 | 12/1993 | Opolski . |
| 5,300,085 | 4/1994 | Yock . |

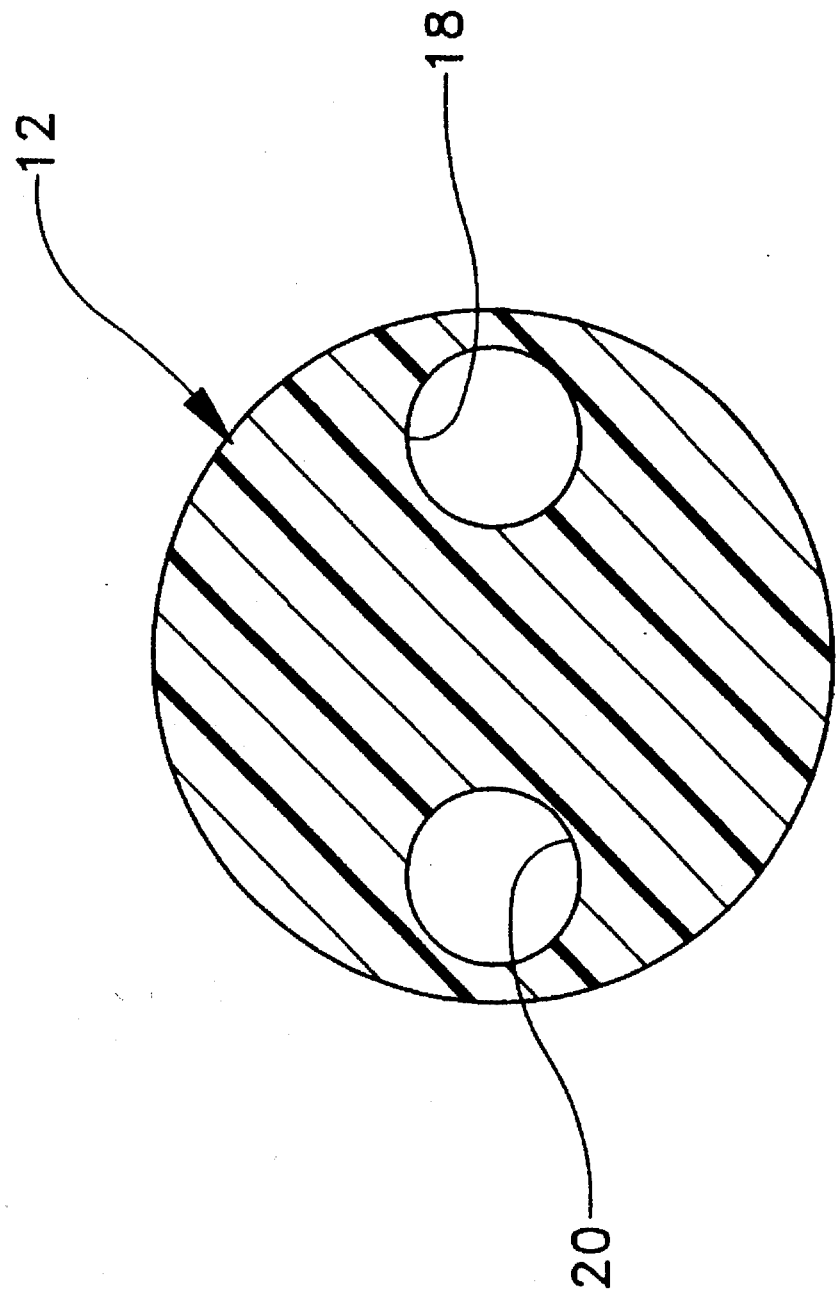

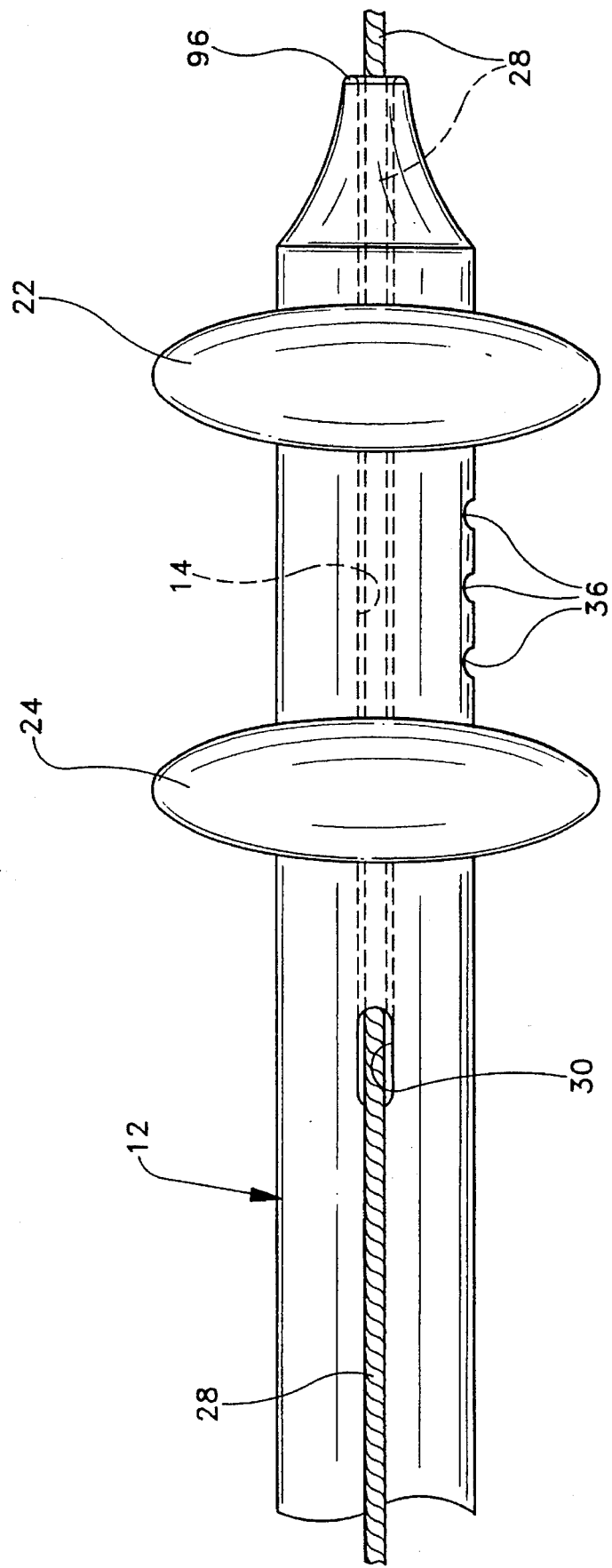

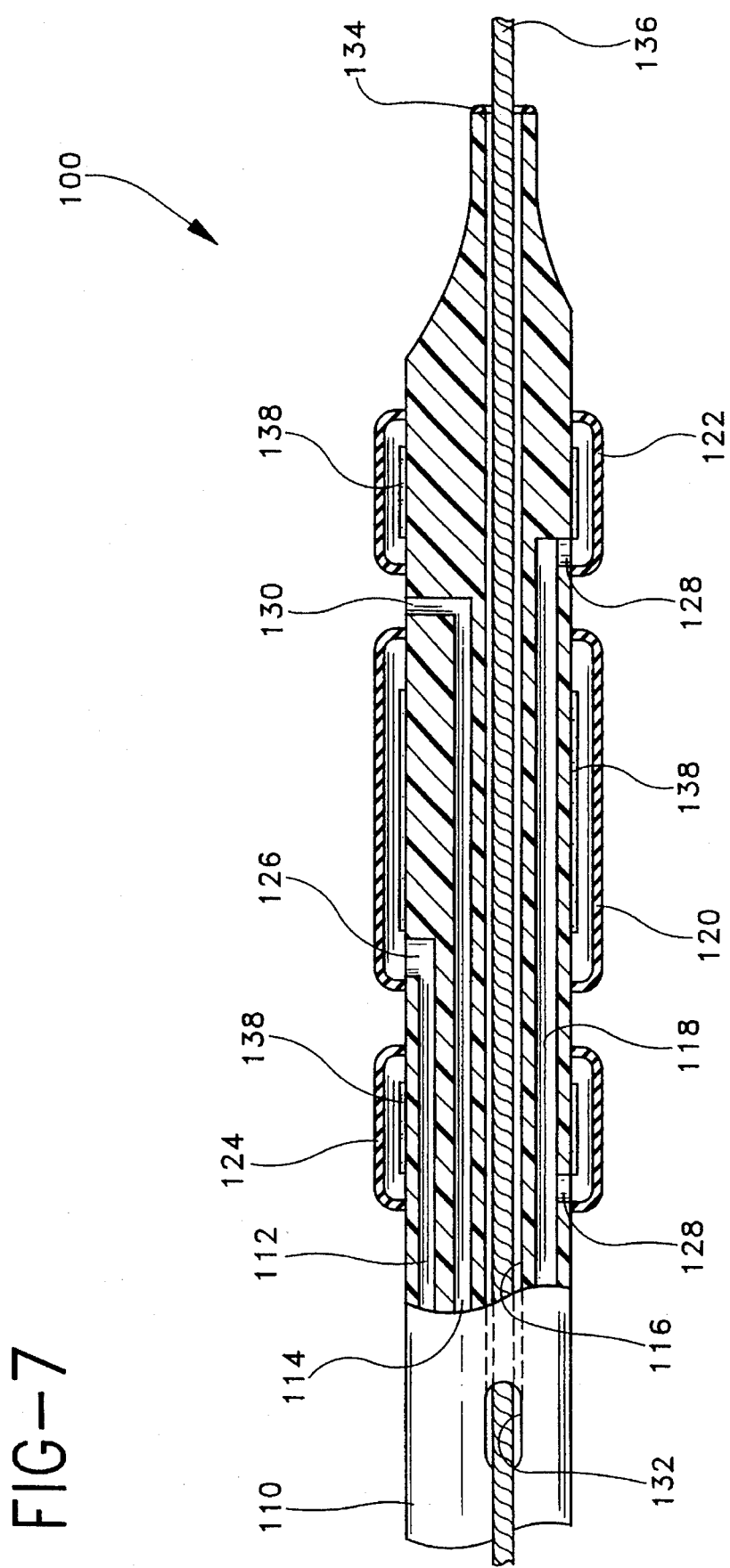

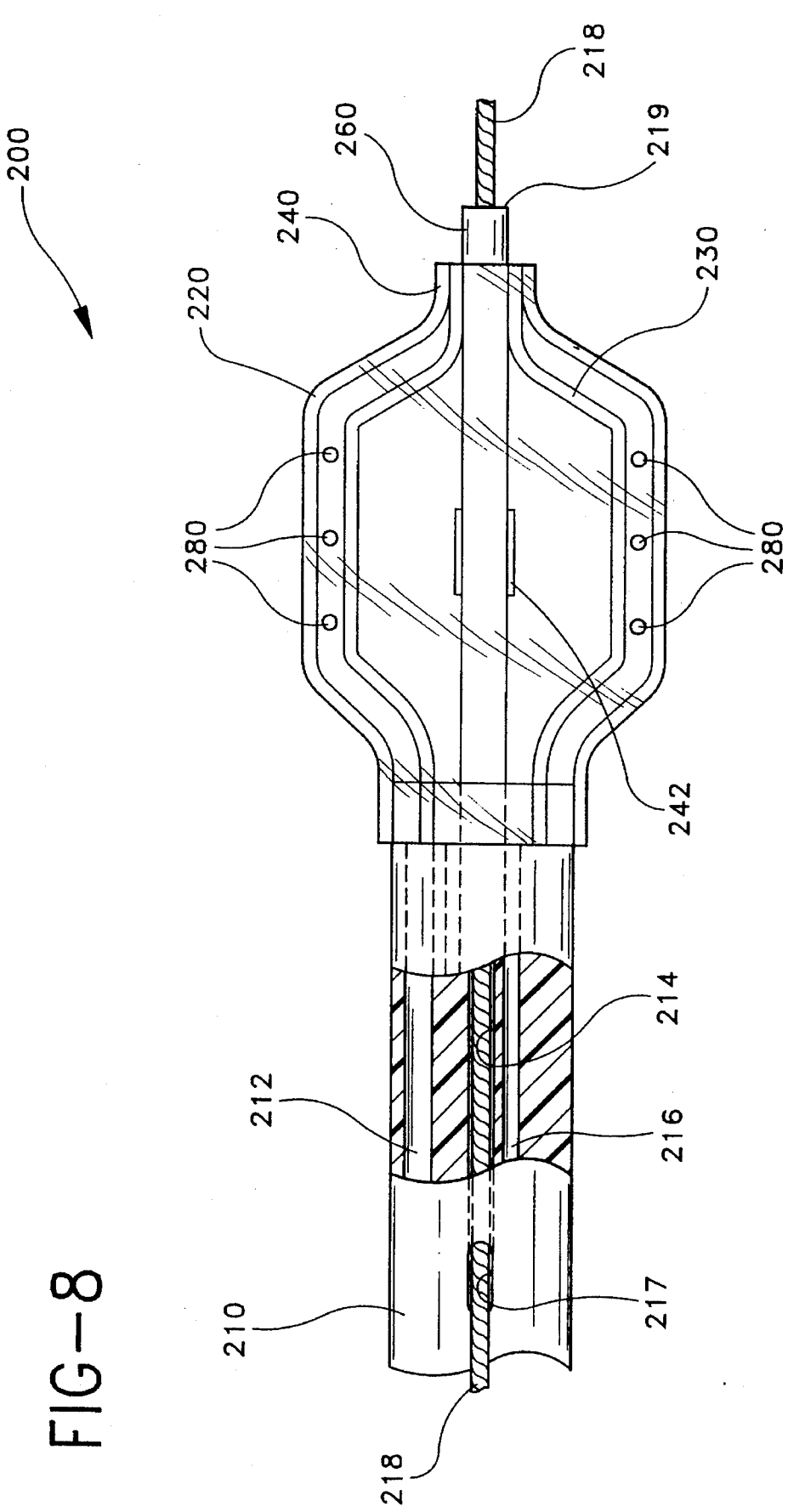

DRUG DELIVERY AND DILATATION-DRUG DELIVERY CATHETERS IN A RAPID EXCHANGE CONFIGURATION

Drug delivery or dilatation-drug delivery catheters with a guide wire lumen terminating within the catheter shaft and an opening to enable the guide wire to exit the catheter shaft.

BACKGROUND OF THE INVENTION

Percutaneous transluminal angioplasty ("PTA") and percutaneous transluminal coronary angioplasty ("PTCA"), wherein a dilatation balloon is advanced through the vascular system to a stenosis and inflated to open the blockage, is now a commonplace procedure. In about one-third of the cases, however, the procedure leads to restenosis that can require another dilatation procedure. It is estimated that the total cost of restenosis requiring an additional dilatation procedure or some other treatment, is over 2 billion dollars per year worldwide.

Various agents that may reduce restenosis can be applied to the dilatation site. For example, antithrombolytic agents such as heparin may prevent clotting. Antiproliferative agents, such as dexamethasone, can prevent smooth muscle cell migration and proliferation.

Various methods have been proposed to effectively deliver such agents to the dilatation site. For example, in U.S. Pat. No. 5,087,244, to Wolinsky, a catheter is disclosed having a thin walled flexible balloon with a plurality of small holes. After an angioplastic procedure, such a balloon can be advanced to the dilatation site and inflated with heparin, or some other medication. The medication exits the inflated balloon, which is in contact with the arterial wall, through the holes.

U.S. Pat. Nos. 4,824,436 and 4,636,195, also to Wolinsky, disclose a catheter with a drug delivery conduit provided between a pair of occlusion balloons. An embodiment is disclosed wherein a dilatation balloon is also provided between the occlusion balloons enabling both dilatation and drug delivery with the same catheter.

Another dilatation-drug delivery catheter is disclosed in U.S. Pat. No. 4,994,033 to Shockey et al. There, a double layered balloon with small holes in its outer layer is provided. Medication is introduced between the two layers and inflation fluid is introduced into the interior portion of the balloon. The pressure of the inflation fluid dilatates the stenosis and forces the medication directly into the tissue being dilatated.

Drug delivery and dilatation-drug delivery catheters are typically advanced to the dilatation site along a guide wire, which is received within a guide wire lumen that extends through the entire shaft of the catheter. Due to frictional forces between the guide wire and the catheter, advancing and removing the catheter can be difficult and time consuming.

In addition, because the entire catheter covers the guide wire, in order to insert or replace an over-the-wire catheter, it is necessary that the guide wire protrude from the patient's body by a length greater than the length of the catheter. Such a guide wire would be about 300 cm. long, and the portion extending from the body would be about 230 cm. Otherwise, the guide wire cannot be secured and its position proximate a lesion cannot be maintained. Instead of such a long guide wire, an exchange wire can be connected to the portion of the guide wire extending from the body when exchanging catheters. Exchange wires need to be at least 180 cm. long.

In either case, additional personnel are needed during the procedure to handle the long wire. Even with the additional personnel, manipulation of the catheters during an exchange can be awkward. The length and expense of the procedure are, therefore, unnecessarily increased.

SUMMARY OF THE INVENTION

In accordance with one embodiment of the invention, a drug delivery catheter is disclosed comprising a catheter shaft having a distal end, at least one drug delivery port proximate the distal end and at least one drug delivery lumen for providing a drug to the drug delivery port. The catheter shaft further comprises a guide wire lumen extending from the distal end of the catheter shaft to a terminus within the catheter shaft. The terminus is proximal to the drug delivery port and defines an opening proximate the terminus for the guide wire to exit the catheter shaft. The catheter shaft, therefore, only covers a portion of guide wire extending from the body, obviating the need for a long guide wire or exchange wire. Occlusion balloons are preferably provided for isolating the site of drug delivery. An additional lumen for perfusion is also preferably provided. The distal end of the perfusion lumen is preferably tapered.

In another embodiment of the invention, a catheter comprises a catheter shaft having a distal portion and a distal end; means for conveying a drug to the exterior of the catheter; means for delivering the drug to the means for conveying; and means for receiving a guide wire within the distal portion of the catheter shaft. The means for receiving includes a means for the guide wire to exit the distal portion of the catheter shaft to an exterior of the catheter shaft.

In another embodiment of the invention, a dilatation-drug delivery catheter is disclosed comprising a catheter shaft with a distal portion, a distal end and a proximal end. A dilatation balloon is attached to the distal portion of the catheter shaft. A first occlusion balloon is attached to the catheter shaft at a location distal to the dilatation balloon and a second occlusion balloon is attached to the catheter shaft at a location proximal to the dilatation balloon. The catheter shaft further comprises at least one drug delivery port in the distal portion of the catheter shaft, between the dilatation balloon and the occlusion balloons. At least one dilatation lumen is provided in fluid communication with the dilatation balloon. At least one inflation lumen is provided in fluid communication with the occlusion balloons. At least one drug delivery lumen is similarly provided in fluid communication with the drug delivery port.

A guide wire lumen is provided in the distal portion of the catheter shaft. The guide wire lumen has a first opening to an exterior of the catheter shaft at the distal end of the catheter shaft and a second opening to the exterior of the catheter shaft in the distal portion of the catheter shaft proximal to the second occlusion balloon and substantially distal to the proximal end of the catheter shaft. A guide wire can enter the catheter shaft through the first opening and exit the catheter shaft through the second opening. As above, since the entire catheter shaft does contain the guide wire, neither a long guide wire nor an exchange wire is required. Furthermore, since dilatation of the stenosis and drug delivery can be provided by the same catheter, problems such as relocating the site of the stenosis after dilatation, and time delays replacing catheters, are avoided.

In another embodiment of a dilatation-drug delivery catheter in accordance with the present invention, a dilatation balloon has an outer and an inner layer attached to the distal portion of a catheter shaft. The inner layer defines an inner region proximate the catheter shaft and the outer and inner layers define an outer region. The outer layer comprises a plurality of openings. A first lumen is in fluid communication with the outer region and a second lumen is in fluid communication with the inner region. A third lumen is provided in the distal portion of the catheter shaft for receiving a guide wire. The third lumen has a first opening to an exterior of the catheter shaft at the distal end of the catheter shaft and a second opening to the exterior of the catheter shaft in the distal portion of the catheter shaft, proximal to the dilatation balloon and substantially distal to the proximal end of the catheter shaft. The guide wire can enter the catheter shaft through the first opening and can exit the catheter shaft through the second opening.

In another embodiment of the invention, a drug delivery balloon with a plurality of ports is attached to the distal portion of a catheter shaft. The catheter shaft further comprises at least one drug delivery lumen in fluid communication with the drug delivery balloon, and a lumen in the distal portion of the catheter shaft for receiving a guide wire. The guide wire lumen has a first opening to the exterior of the catheter shaft at the distal end of the catheter shaft and a second opening to the exterior of the catheter shaft in the distal portion of the catheter shaft, proximal to the drug delivery balloon and substantially distal to the proximal end of the catheter shaft. Once again, the guide wire can enter the catheter shaft through the first opening and exit the catheter shaft through the second opening. A lumen for perfusion is also preferably provided. The perfusion lumen preferably has a tapered end.

DESCRIPTION OF THE DRAWINGS

FIG. 5 is a cross-sectional view of the proximal portion of the catheter of FIG. 1, along line 5—5 of FIG. 1;

FIG. 6 is a plan view of the catheter of FIG. 3, with the occlusion balloons inflated;

FIG. 7 is a partial plan, partial cross-sectional view of the distal portion of a second embodiment of the present invention;

FIG. 8 is a partial plan, partial cross-sectional view of the distal portion of a third embodiment of the present invention.

DESCRIPTION OF THE INVENTION

Figure 1:
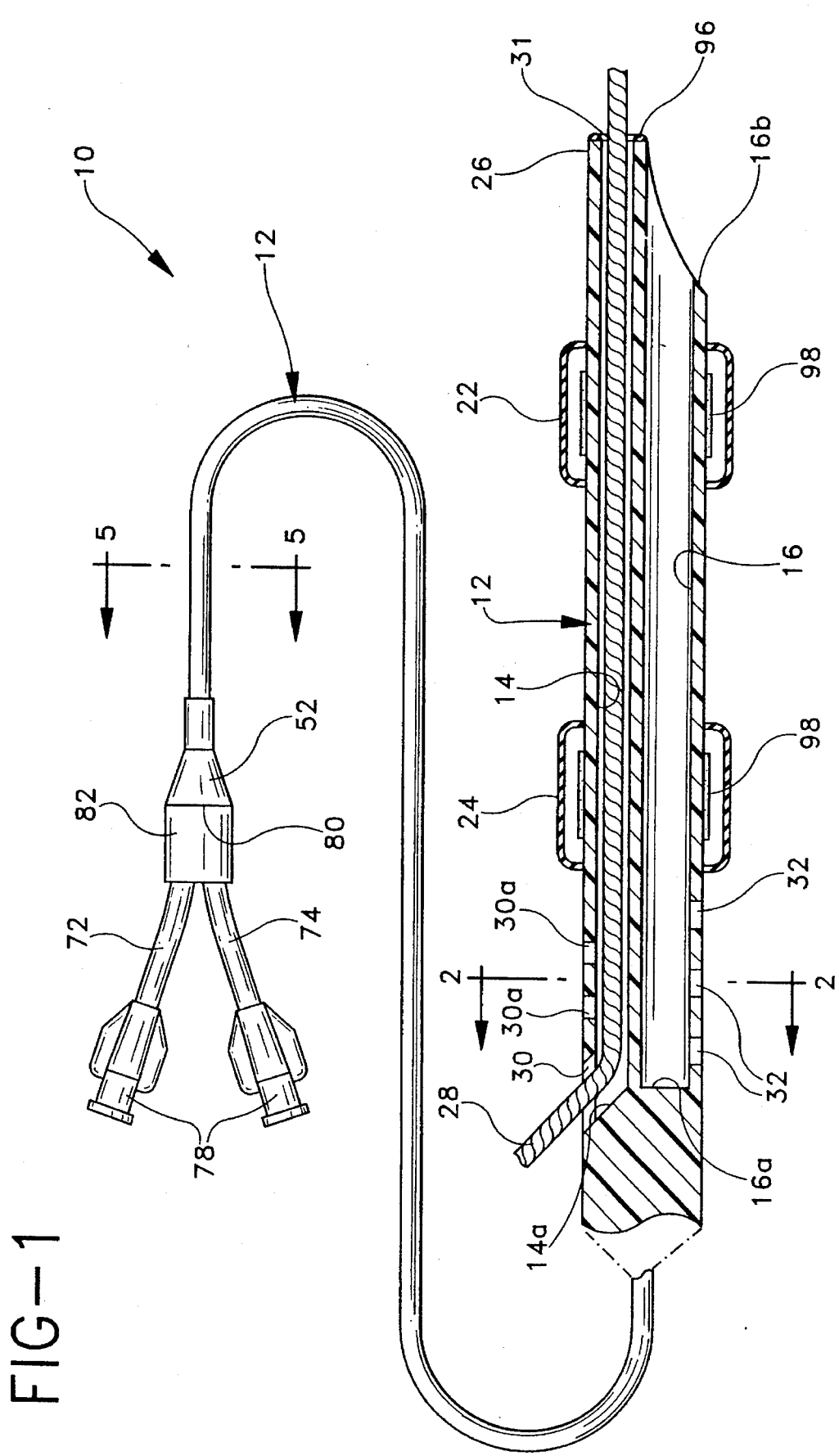
FIG. 1 is a view of a drug delivery catheter in accordance with one embodiment of the present invention, wherein the distal portion of the catheter is shown enlarged and in cross-section.

FIGS. 1–6 illustrate one embodiment of a drug delivery catheter 10 in accordance with the present invention. In FIG. 1, the distal portion of the catheter 10 is shown enlarged and in cross-section. The catheter 10 comprises a catheter shaft 12. Two occlusion balloons 22 and 24 are preferably attached to the distal portion of the catheter shaft 12. A first lumen 14, which extends from the distal end 26 of the catheter shaft 12 to a terminus 14a proximal the occlusion balloon 24, is provided to receive a guide wire 28. An opening 30 is provided in the wall of the catheter shaft 12 proximate the terminus. The first lumen 14 is preferably located proximate the periphery of the catheter shaft 12. The guide wire 28 can enter the catheter shaft 12 through an opening 31 in the first lumen 14 at the distal end 26 of the catheter shaft 12, and exit through the opening 30. The opening 30 is substantially distal of the proximal end of the catheter 10. The diameter of the first lumen can be about 0.022 inches. The distal end of the guide wire 28 extends out of the distal end of the lumen 14 during use, as shown in FIG. 1. The distance between the distal end of the catheter and the opening 30 is preferably about 5–25 cm. The total length of the drug delivery catheter 10 can be from 120–160 cm, although longer or shorter lengths are possible. Allowing the guide wire 28 to exit the catheter shaft 12 through the opening 30 eliminates the need for excessively long guide wires or the use of exchange wires, because when removed from the body, only a portion of the guide wire extending from the body is covered by the catheter 10. There is, therefore, sufficient room on the guide wire to hold it in position, as the catheter 10 of the invention is inserted or removed from the body. With the catheter 10 of the present invention, it is only necessary for the guide wire 28 to extend about 75 cm. from the body.

A second lumen 16 also preferably extends from the distal end 26 of the catheter shaft 12 to a terminus 16a proximal to the occlusion balloon 24. The diameter of the second lumen can be about 0.013 inches. A plurality of ports 32 preferably extends through the wall of the catheter shaft 12 to the second lumen 16, enabling the passive perfusion of blood through the lumen 16, as discussed further, below. There are preferably between 2–20 circular or oval ports 32 with a diameter or length, respectively, of between about 0.003–0.020 inches. Three perfusion openings 32 are provided in this embodiment. Ports 30a can also be provided between the proximal occlusion balloon 24 and the opening 30, through to the first lumen 14, to enable perfusion of blood through that lumen as well. The distal end 16b of the second lumen 16 is preferably tapered, as shown in FIG. 1. This makes the opening of the distal end 16b difficult to see, making it unlikely that the guide wire 28 will be inserted into the second lumen 16 instead of the first lumen 14 during use. Alternatively, the lumen 16 can extend through the entire length of the catheter shaft 12, enabling active perfusion of blood or perfluorochemicals, as is known in the art, and discussed further below.

Figure 2:
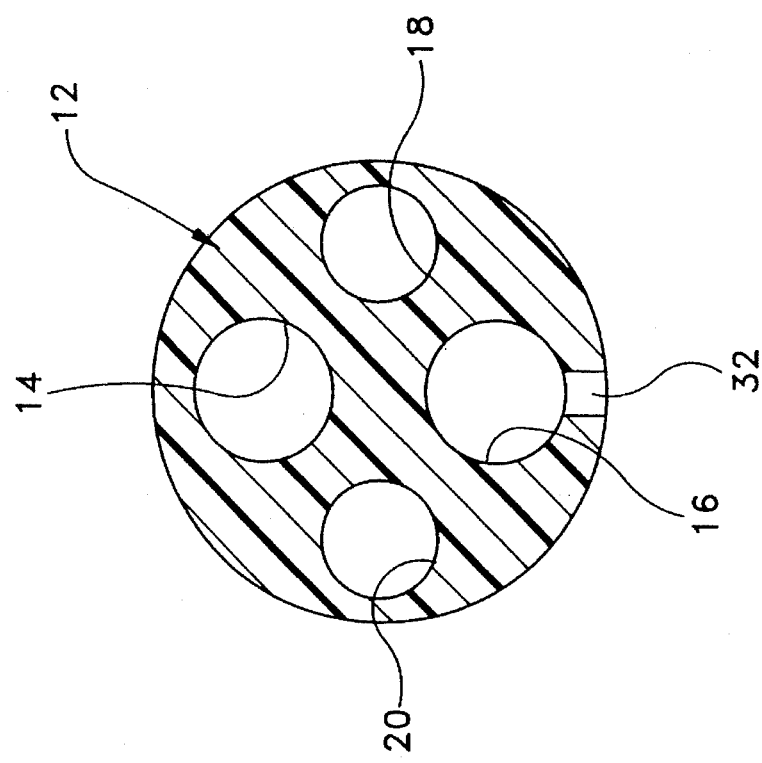
FIG. 2 is a cross-sectional view of the distal portion of the catheter of FIG. 1, along line 2—2 FIG. 1.
Figure 3:
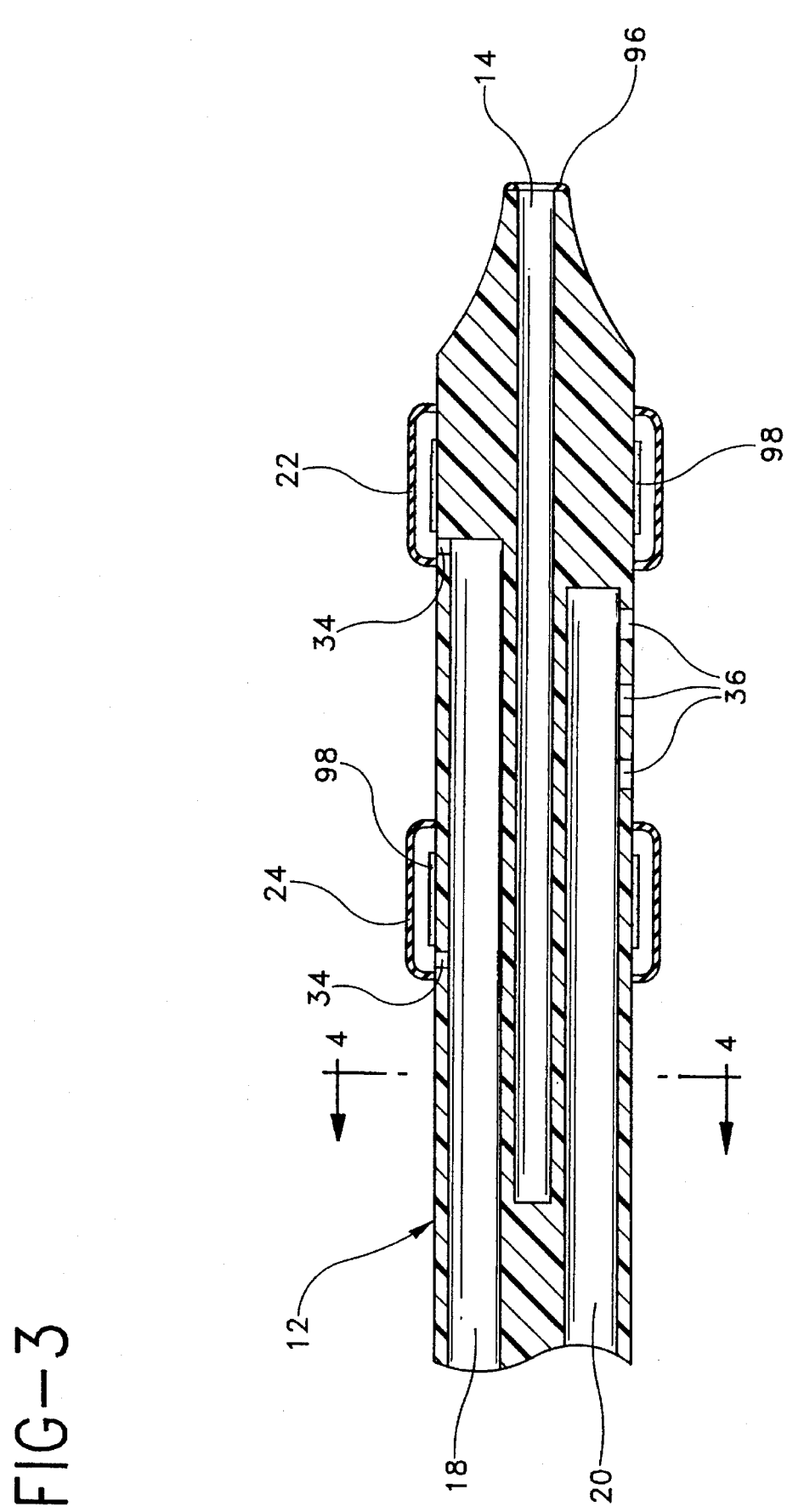
FIG. 3 is a cross-sectional view of the distal portion of the catheter of FIG. 1, rotated 90°.

FIG. 2 is a cross-sectional view of FIG. 1 through line 2—2, showing the first and second lumens 14 and 16, and a port 32, as well as third and fourth lumens 18 and 20, which are discussed with respect to FIG. 3.

FIG. 3 is a cross-sectional view of the distal portion of the catheter 10, rotated 90°. The guide wire 28 is not shown. In this view, the third lumen 18 is shown, which provides inflation fluid to the occlusion balloons 22, 24 through ports 34 extending through the catheter shaft 12. Preferably, a single lumen 18 is used to inflate both occlusion balloons 22, 24. The diameter of the third lumen 18 can be about 0.010 inches. Separate lumens for each balloon 22, 24 can be provided, as well.

Figure 4:
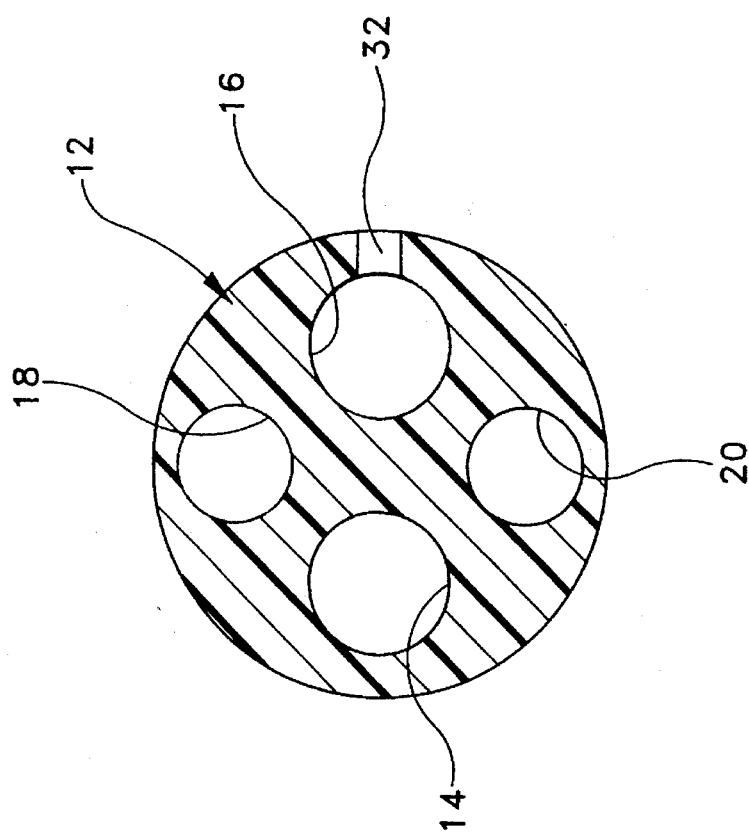
FIG. 4 is a cross-sectional view of the distal portion of the catheter of FIG. 3, along line 4—4 of FIG. 3.

A fourth lumen 20 for delivering medication is also shown. At least one drug delivery port 36 is provided between the occlusion balloons, through the catheter shaft 12, to the fourth lumen 20. The diameter of the fourth lumen can be about 0.010 inches. There are preferably between 2–20 circular or oval shaped ports 36 with a diameter or length, respectively, of between about 0.003–0.020 inches, to ensure the delivery of adequate drug to the dilatation site. Three such ports are shown in FIG. 3. Any desired medication can be delivered to the dilatation site, through the fourth lumen 20. FIG. 4 is a cross-sectional view of the catheter shaft 12 through line 4—4 of FIG. 3 showing the orientation of the lumens in that view. Additional drug delivery lumens may be provided, as well.

The occlusion balloon 22, 24, are preferably provided to isolate the dilatation site during drug delivery. The occlusion balloons 22, 24 maintain the drug in proximity with the portion of the arterial wall which has been dilatated, improving the absorption and efficacy of the drug. FIG. 6 is a plan view of the catheter 10 in the orientation of FIG. 3, showing the occlusion balloons 22, 24, inflated as they would be immediately prior to and during drug delivery. The opening 30 and the exiting guide wire 28, along with the drug delivery ports 36, are also shown. The perfusion openings 32 are on the far side of the catheter in this view.

Instead of an integral catheter shaft 12 with multiple lumens, the catheter shaft 12 can comprise a plurality of tubes appropriately bonded together. In addition, the distal portion of the catheter shaft 12, shown enlarged in FIG. 6 can be of a softer material than the remainder of the shaft. The softer material of the distal portion eases maneuvering through the vascular system while the harder material of the remainder of the shaft provides better pushability. The two portions can be simply attached by thermal bonding or an adhesive, as is known in the art. Suitable materials are discussed below. A stainless steel or tungsten wire (not shown) can also be provided in the proximal portion of the catheter shaft 12, to further improve the stiffness and pushability of the catheter 10.

Returning to FIG. 1, the proximal end of the catheter 10 includes two tubes 72 and 74 which are connected to the catheter shaft 12. One tube is connected to the third lumen 18, for the delivery of inflation fluid. The other tube is connected to the fourth lumen 20, for the delivery of medication. Hubs 78 are connected to each tube. Syringes can be used to supply the inflation fluid for the occlusion balloons 22, 24 and any desired drug through the tubes 72 and 74. If the catheter 10 is to be adapted for active perfusion and the second lumen 16 extends to the proximal end of the catheter shaft 12, a third tube (not shown) can be attached to the second lumen 16. If additional lumens are provided, additional tubes can be attached to the catheter shaft 12 or a Y-adapter can be provided. FIG. 5 is a cross-sectional view of the catheter shaft along line 5—5 of FIG. 1, showing the third lumen 18 and fourth lumen 20.

The outer diameter of the catheter 10 and the deflated occlusion balloons 22, 24 is preferably no greater than about 0.056 inches, so that it can be used with a 7 or 8 French guiding catheter.

To accommodate the tubes 72 and 74 the proximal end of the inner catheter shaft 52 flares to an outer diameter of about 0.140 inches at about point 80. The tubes 72 and 74 are held together by a heat shrink tubing 82. The tubes 72, 74 can be connected to the catheter shaft by thermal bonding or an adhesive.

The distal end 26 of the first lumen 14 preferably includes a resilient tip 96 which comprises a material softer than that of the catheter shaft 12. The tip 96 spreads or bends when it contacts body tissue, easing the catheter's passage through the vascular system and helping to avoid tissue damage. The tip 96 can be made of ultra low density polyethylene 4603 from Dow Chemical Corporation, which has a melt flow rate at 190° C. (ASTM D-1238) of 0.7–0.9 g/10 min. and a density (ASTM D-792) of 0.9030–0.9070 g/cc. The tip 96 can also be a nylon or polyamide copolymer, such as PEBA 25D from Elf Atochem Deutschland GmbH, which has an ultimate tensile strength (ASTM D-638) of 4950 psi minimum ("min."), an ultimate elongation (ASTM-638) of 640% min., a flexural modulus (ASTM D-790) of 2100 psi min., a Durometer (ASTM D-2240) of 25D±4D, and a melting point (ASTM D-3418) of 142°–153° C. The tip 96 can be connected to the catheter shaft 12 by an adhesive or thermal bonding.

Radiopaque markers 98 of gold or tantalum, for example, are also preferably provided on the catheter shaft 12 within the occlusion balloons 22, 24, as shown, to assist in monitoring the position of the catheter on a fluoroscope during a PTA or PTCA procedure, as is known in the art. Such markers can be provided at other locations, such as proximal to the rearmost port 32, as well.

The catheter shaft 12 and occlusion balloons 22, 24, are preferably coated with a lubricous material, such as silicone, acrylimide, or a hydrophilic polyurethane coating, to ease passage of the drug delivery catheter 10 of the invention through the guiding catheter, as is known in the art.

The catheter shaft can be of any material suitable for catheters, such as linear low density or high density polyethylene, nylon, polyamide, polyamide copolymer, polyurethane, polypropylene, polyester copolymer, silicone rubber, or other non-thrombogenic materials. Metallic tubing, such as stainless steel or Nitinol, a nickel-titanium alloy available from Raychem Corporation, for example, can also be used.

An appropriate linear low density polyethylene is Dowlex 2038 from Dow Chemical Company, which has a melt flow rate at 190° C. (ASTM D-1238) of 0.85–1.15 g/10 min. and a density (ASTM D792) of 0.9330–0.9370 g/cc. A high density polyethylene which can be used is LB 8320-00 from Quantum Chemical Corporation, which has a melt flow rate at 190° C. (ASTM D-1238) of 0.20–0.36 g/10 min. and a density (D-1505) of 0.9566 g/cc min.

A nylon which can be used is nylon 12, such as L2101F Vestamed from Hüls America Inc., which has a relative viscosity (ISO 307) of 2.05–2.22 and a water content (ASTM D-4019) of 0.10 maximum. Another nylon which can be used is PEBA 70D from Elf Atochem, which has an ultimate tensile strength (ASTM D-638) of 8300 psi min., an ultimate elongation (ASTM D-638) of 400% min., a flexural modulus (ASTM D-790) of 67,000 psi min., a Durometer (D-2240) of 69D±4D and a melting point (ASTM D-3418) of 160°– 180° C.

A high density polyethylene which can be used is LM6007 from Quantum Chemical Corporation, which has the following characteristics:

| | |
|---|---|
| Ultimate Tensile Strength (ASTM D-638) | 4400 psi min. |
| Ultimate Elongation % at break (ASTM D-638) | 600% min. |
| Durometer D Scale (ASTM D-2240) | 68 ± 4.5 |
| Melt Flow Rate at 240° C. 2160 g (ASTM D-1238) | 0.070 (REF) |
| Flexural Modulus at Room Temperature (ASTM D-790, Procedure B) | 220,000 psi min. |
| Vicat Softening Point °C. (ASTM D-1525) | 125° C. (REF) |

If it is desired that the distal portion of the catheter shaft 12 be softer than the remainder of the shaft, one appropriate nylon that can be used is PEBA 63D from Elf Atochem, which has an ultimate tensile strength (ASTM D-638) of 8100 psi min., an ultimate elongation (ASTM D-638) of 300% min., a flexural modulus (ASTM D-790) of 49,000 psi min., a durameter (ASTM D-2240) of 63D±4D and a melting point (ASTM D-3418) of 160°–180° C.

The catheter shaft 12 with the desired number of lumens can be made by conventional extrusion processes. To form the flared portion of the catheter shaft 12, a bump extrusion process can be used, as is known in the art. Instead of an integral catheter shaft 12 with lumens, separate tubes can be provided and bonded together, as well.

The resilient tip 96 can be attached to the catheter shaft by placing a small tube of the tip material over the distal end of the catheter shaft 12 and thermally bonding it into place. An adhesive can be used, as well. The tube material can increase the outer diameter of the catheter shaft 12. To maintain the outer diameter of the catheter shaft 12 less than about 0.056 inches after placement of the tube of tip material, the distal portion of the catheter shaft can be reduced or "necked-down" an appropriate amount prior to attachment of the tip material. To maintain the lumens 14 and 16 open while the resilient tip is attached by thermal bonding, mandrels are inserted into each lumen. The tube of tip material can extend to the region of the catheter shaft 12 where the distal occlusion balloon 22 is attached. All or a portion of that balloon would then be attached to the tip material.

During thermal bonding of the tip material, the distal portion of the third and fourth lumens 18, 20 close. If it is necessary to close a greater portion of either lumen, a small, solid tube of the same material as the catheter shaft 12 is inserted into the proximal end of that lumen and thermally bonded into place. Adhesive may be used as well. The outer diameter of the tube is preferably slightly greater than the diameter of that lumen. The mandrels are maintained in the other lumens to keep them open. If the third lumen 18 does not close during attachment of the resilient tip 96, it can be closed in the same way as the fourth lumen.

The proximal portions of the first and second lumen 14, 16, can be similarly sealed.

The occlusion balloons 22, 24 can be nylon, polyamide, polyamide copolymer, polyethylene, polyethylene terephthalate, polyester elastomers, polyurethane, Kraton, silicone, latex or any other soft, non-thrombogenic material which will seal against, but not expand, the arterial wall when inflated. The balloons can be tubes which expand on inflation or blow molded balloons. If the balloon material is compatible with the catheter shaft 12, the occlusion balloons 22, 24 can be attached by thermal bonding techniques, including laser bonding. An apparatus and process for laser bonding balloons onto catheters is disclosed in U.S. Pat. No. 5,267,959, which is incorporated by reference herein. An adhesive may be used, as well. A nylon which can be used for the occlusion balloons 22, 24 is L25 G Grilamid from EMS-Chemie AG, which has a melting point of 178° C., a density (DIN 53479) of 1.01 Kg/dm$^3$, a tensile strength (DIN 53455) of 40 N/mm$^2$, an elongation at yield (DIN 53455) of 10% and a Shore D hardness (DIN 53505) of 72.

The drug delivery catheter of the first embodiment of the present invention can be used to deliver medication to the site of the PTA or PTCA procedure after dilatation is performed in an ordinary manner. The dilatation catheter, which is preferably of a rapid exchange format as described in U.S. Pat. No. 4,762,129 to Bonzel, for example, which is incorporated by reference herein, is first removed. The drug delivery catheter 10 of the present invention can then be introduced into the vascular system and advanced to the dilatation site through a guiding catheter, along the same guide wire along which the dilatation catheter was advanced to the stenosis. No exchange wire is necessary and the guide wire needs to extend only about 75 cm. from the body. The distal end of the first lumen 14 of the catheter 10 is inserted into the guide wire, such as the guide wire 28 in FIG. 1. As the catheter 10 is advanced along the guide wire, the guide wire exits the catheter 10 from the opening 30. The catheter 10 continues to track along the portion of the guide wire within the first lumen 14 as it is advanced to the dilatation site.

The progress of the catheter 10 is followed on a fluoroscope. When the dilatation site is reached, the occlusion balloons 22, 24 are inflated though the third lumen 18 until the occlusion balloons 22, 24 meet and seal against the arterial wall. If perfusion openings 32 and 30a are present, blood will then flow through the second lumen 16 and first lumen 14, respectively, out the distal end of the catheter 10. If the catheter 10 is configured to allow active perfusion (i.e., if the second lumen 16 extends the full length of the catheter shaft 12), blood or perfluorochemicals such as Fluosol® can be injected with a syringe through tube 76, as is known in the art.

Antithrombolytic, antiproliferative, or any other type of drug, can now be injected through tube 72, the fourth lumen 20 and drug delivery ports 36, via a syringe, to the dilatation site. One drug formulation which may be promising is dexamethasone absorbed in poly-lactic/poly-glycolic particles with diameters substantially less than 100 microns. Such particles can adhere to or penetrate the arterial wall. The surface of the particles can be treated with cell adhesion proteins and peptides based peptides to improve the adhesion of the particles with the arterial wall. An arginine glycine aspartic acid based peptide which can be used is Peptite 2000® from Telios Pharmaceuticals, INC.

After the drug has been applied at the desired pressure and for the desired length of time (typically from about 20 seconds to 3 minutes), the occlusion balloons are deflated and the drug delivery catheter 10 is quickly and easily withdrawn from the blood vessel.

FIG. 7 is a partial cross-sectional, partial plan view of a second embodiment of the present invention, wherein the catheter 100 provides both dilatation and drug delivery. The catheter 100 comprises a catheter shaft 110 including a first lumen 112, a second lumen 114, a third lumen 116 and a fourth lumen 118. A dilatation balloon 120 and two occlusion balloons 122, 124 are attached to the catheter shaft 110. The dilatation balloon 120 is in fluid communication with the first lumen 112 through an opening 126. The occlusion balloons are similarly in fluid communication with the fourth lumen 118 through openings 128. A port 130 is provided through the wall of the catheter shaft 110 to the second lumen 114, through which medication can be provided to the dilatation site. As above, additional drug delivery lumens can be provided. Additional lumens can be provided to deliver fluid to the dilatation balloon 120 or occlusion balloons 122, 124, as well. An opening 132 is also provided through the wall of the catheter shaft 110 to the third lumen 116. The third lumen, which extends through an opening 133 in the distal end 134 of the catheter 100, receives the guide wire 136, which exits the lumen 116 through the opening 132. An additional lumen (not shown) may also be provided for active or passive perfusion. The distal end of such a perfusion lumen would be preferably tapered, as discussed above. A lubricous coating, as discussed above, is also provided on the dilatation balloon 120, as well as the remainder of the catheter 100. As above, instead of an integral catheter shaft with multiple lumens, the catheter shaft 110 can comprise a plurality of tubes appropriately bonded together.

The dilatation balloon 120 can be of any type and size appropriate for PTA and PTCA procedures. For example, the balloon 120 can be of polyethylene, polyethylene terephthalate, nylon, polyamide, polyamide copolymer, polyurethane, or any other material suitable for a dilatation balloon. The balloon 120 can be compliant, non-compliant, or semi-compliant. The dilatation balloon 120 can be attached to the catheter shaft 110 through thermal bonding, including laser bonding or ultrasonic bonding, or with an adhesive, as is known in the art. The balloon 120 is preferably of the same or compatible material as the catheter shaft 110, to enable thermal bonding.

A low density polyethylene which can be used for the dilatation balloon 120 is P.E. 1031 from Rexene Corporation, which has a melt flow rate at 190°±0.2° C. (ASTM D-1238) of 0.4–1.4 g/10 min., a density (ASTM D-1505) of 0.93±0.02 g/cc and a melt point (ASTM D-3417, D-3418) of 104°–140° C. A linear low density polyethylene which can be used is Dowlex 2247A LLPDE from Dow Chemical Corporation, which has a melt index at 190° C./2.16 kg (ASTM D-1238) of 2.0–2.6 g/10 min., a density (ASTM D-1505) of 0.9150–0.9190 g/cc, and a melt point (D-3417, D-3418 (REF)) of 122°–125° C.

The materials discussed above with respect to the first embodiment are appropriate for other corresponding components of this embodiment. As in the first embodiment, radiopaque markers 138 are provided on the catheter shaft 110 beneath the dilatation balloon 120, as well as the occlusion balloons 122, 124. The proximal end of the catheter 100 can be essentially the same as the proximal end of the catheter 10 in FIG. 1, except that a third tube would be attached to the proximal end of the catheter shaft 110, for supplying dilatation fluid to the dilatation balloon 120, through the first lumen 112. A Y-adapter may be used as well, as is known in the art.

In use, the catheter 100 of this embodiment would be inserted onto a guide wire, such as the guide wire 136, which has been advanced through a guiding catheter to the site of a stenosis, as is known in the art. The guide wire can enter the catheter 100 through the opening 133 and exit the third lumen 116 through the opening 132. As above, since only a portion of the catheter 100 is in frictional engagement with the guide wire, the catheter can be easily and quickly advanced to the stenosis and a short guide wire can be used. When properly positioned, the dilatation balloon 120 can be inflated to open the stenosis in a conventional manner. The dilatation balloon 120 can then be deflated and the occlusion balloons 122, 124 can be inflated, as discussed above. Any desired medication can then be delivered through the second lumen 114. By enabling both dilatation and drug delivery by the same catheter, this embodiment lessens the length of the procedure by eliminating the time required to remove a dilatation catheter and insert a separate drug delivery catheter. In addition, it alleviates the problem of precisely relocating the dilatation site for proper positioning of the drug delivery catheter.

In a third embodiment of the present invention, the catheter 200 can both dilatate a stenosis and deliver drug to the dilatation site, through the same dilatation balloon. FIG. 8 shows a partial cross-sectional, partial plan view of the distal portion of such a catheter 200, with the dilatation balloon expanded. The catheter comprises a catheter shaft 210, a first lumen 212, a second lumen 214 and a third lumen 216. The second lumen 214 receives the guide wire 218 through an opening 219. An opening 217 is provided though the catheter shaft 210 to the second lumen 214, to provide an exit for the guide wire 218. Instead of an integral catheter shaft with multiple lumens, the catheter shaft 210 can comprise a plurality of the tubes appropriately bonded together, as well.

The balloon portion of the catheter 200 comprises an outer balloon 220 and an inner balloon 230. The second lumen 214 extends through the interior of the inner balloon 230. The distal end of the outer balloon 220 is thermally or adhesively bonded to the distal end of the inner balloon 230, which in turn is thermally or adhesively bonded to the exterior surface of the second lumen 214, at 240.

The proximal ends of the outer balloon 220 and inner balloon 230 are thermally or adhesively bonded to the catheter shaft 210 such that the region between the outer and inner balloons is in fluid communication with the first lumen 212, while the interior of the inner balloon 230 is in fluid communication with the third lumen 216. Inflation fluid is provided through the third lumen 216 and medication is provided through the first lumen 212. A plurality of micropores 280 is formed through the wall of the outer balloon 220 for the medication to exit the balloon. Such pores can be between 0.01 microns–0.1 mm. Where the outer layer 280 of the balloon 220 comprises a biaxially oriented plastic material such as polyethylene terephthalate or nylon or polyester elastomer, the micropores 28 may be formed using a precision laser.

In use, the guide wire 218 would conventionally be routed through a guide catheter and across the lesion to be treated. The distal end 260 of the second lumen 214 is fitted over the proximal end of the guide wire 218. As in the embodiments above, the guide wire exits the catheter 200 through the opening 217. The catheter 200 continues to advance along the portion of the guide wire within the second lumen 214, until the balloon portion is juxtaposed with the lesion to be treated. While in FIG. 8 the inner and outer layers 230, 220 of the balloon are shown in their inflated configuration, those layers would tightly conform to the exterior of the lumen 214 while being advanced to the stenosis.

Once the distal end of the catheter 200 is appropriately positioned with the aid of a radiopaque marker band 242, the selected medication is introduced through the first lumen 212 and into the region between the outer balloon 220 and inner balloon 230. The injection of the drug will cause some enlargement of the outer balloon 220 but typically the pressure at which the drug material is injected is below the point where substantial amounts of the drug are ejected out through the micropores 28. To perform the simultaneous medication delivery and dilatation, an inflation fluid is next injected through the third lumen 216 into the interior of the inner balloon 230. As the pressure is increased, typically approaching seven to ten atmospheres, the inner layer 230 of the balloon inflates to its predetermined maximum diameter and, in doing so, forces the drug through the ports 280 to effectively spray the lesion being treated with the particular drug. The expansion of the inner balloon 230 also results in pressure being exerted against the lesion, forcing it against the vessel wall as the drug is delivered.

Figure 9:
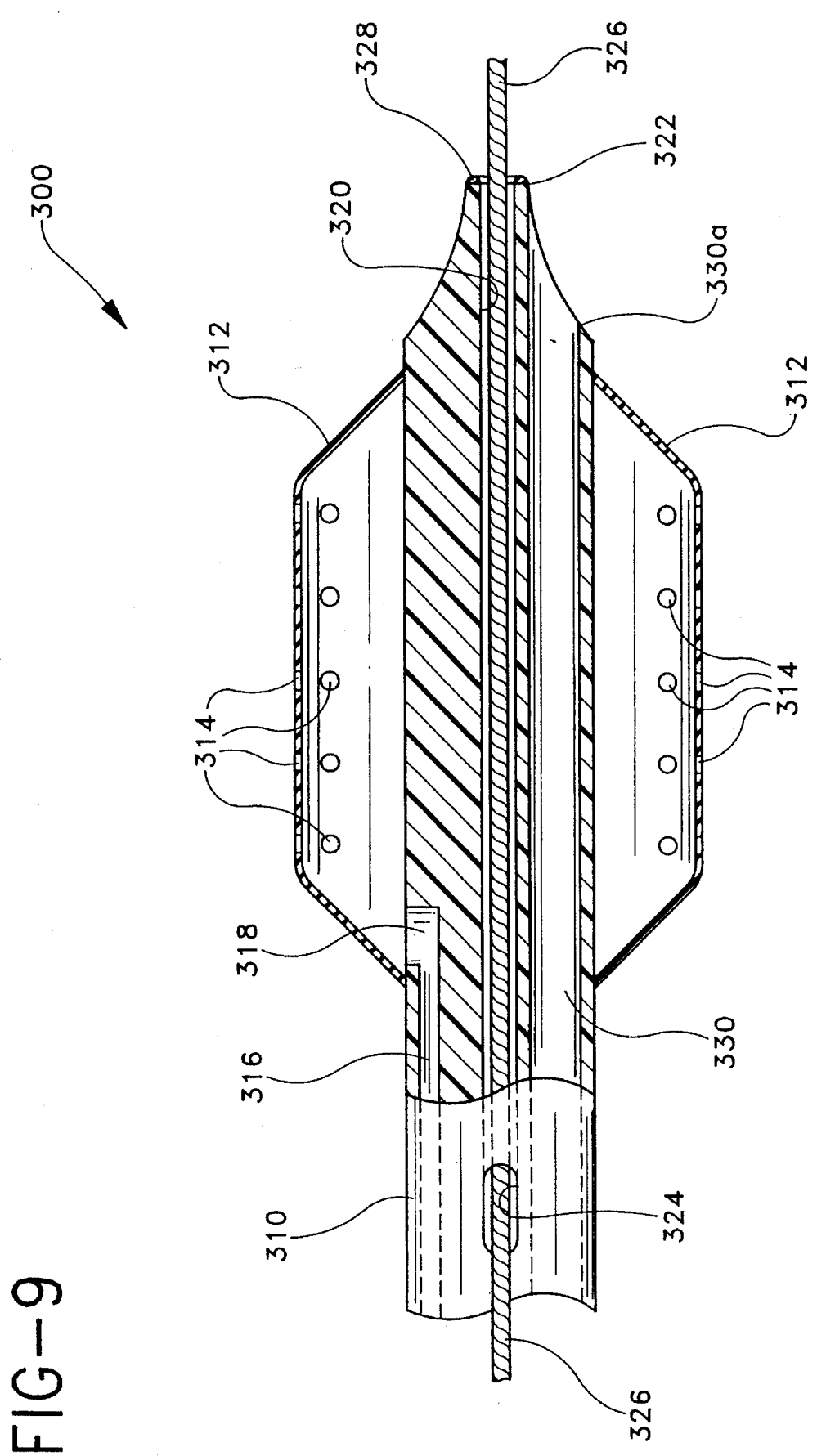
FIG. 9 is a partial plan, partial cross-sectional view of a fourth embodiment of the present invention.

The use of a balloon to deliver drugs to a dilatation site by a drug delivery catheter in accordance with the present invention, is shown in the fourth embodiment of FIG. 9. The catheter 300 comprises a drug delivery balloon 312, which is thermally or adhesively attached to a catheter shaft 310, as described above. In FIG. 9, the balloon 312 is shown in an inflated position. A plurality of drug delivery ports 314 are provided throughout the balloon 312. The balloon 312 is in fluid communication with a drug delivery lumen 316, through a port 318 through the wall of the catheter shaft 310. Additional drug delivery lumens may be provided, as well. A guide wire lumen 320 is provided in the distal portion of the catheter shaft 310, extending from a distal end 322. The guide wire lumen 320 terminates in the distal portion of the catheter shaft 310, proximal to the drug delivery balloon 312. An opening 324 is provided in the wall of the catheter shaft 310, through to the guide wire lumen 320. A guide wire 326 can be inserted through an opening 328 in the distal end 322 of the catheter shaft 310, and exit through the opening 324.

A perfusion lumen 330, with a tapered end 330a, is also preferably provided. This lumen can extend through the entire length of the catheter shaft 310 enabling active perfusion, as discussed above. Alternatively, it can terminate proximal to the drug delivery balloon 312. Openings (not shown) would then be provided through the wall of the catheter shaft 310, as in the first embodiment, to enable passive perfusion. Instead of an integral catheter shaft with lumens, the catheter shaft 310 can comprise a plurality of tubes appropriately bonded together, as well.

The drug delivery and dilatation-drug delivery catheters of the present invention enable quick and easy advance and withdrawal of the catheters, shortening the time required for the procedure. It also eliminates required personnel and equipment, decreasing the cost of the procedure.

While preferred embodiments of the present invention are described above, they are not meant to limit the scope of the invention, which is defined by the following claims.

I claim:

1. A drug delivery catheter comprising:
   a catheter shaft comprising a proximal end, a distal end, at least one drug delivery port proximate the distal end and at least one drug delivery lumen for providing a drug to the drug delivery port, the at least one drug delivery lumen in fluid communication with the proximal end,
   the catheter shaft further comprising a guide wire lumen extending from the distal end of the catheter shaft to a terminus within the catheter shaft, the terminus being proximal to the drug delivery port, and defining an opening proximate the terminus for the guide wire to exit the catheter shaft.

2. The drug delivery catheter of claim 1, further comprising a first occlusion balloon distal to the drug delivery port, and an inflation lumen in fluid communication with the first occlusion balloon.

3. The drug delivery catheter of claim 2, further comprising a second occlusion balloon proximal to the drug delivery port, wherein the terminus of the guide wire lumen is proximal to the second occlusion balloon.

4. The drug delivery catheter of claim 3, wherein the inflation lumen is in fluid communication with the first and second occlusion balloons.

5. The drug delivery catheter of claim 1, wherein there are a plurality of drug delivery ports in fluid communication with the drug delivery lumen.

6. The drug delivery catheter of claim 1, further comprising a lubricous coating on the catheter shaft.

7. The drug delivery catheter of claim 3, further comprising a lubricous coating on the catheter shaft and the occlusion balloons.

8. The drug delivery catheter of claim 3, wherein the occlusion balloons comprise inflatable plastic tubes.

9. The drug delivery catheter of claim 3, wherein the occlusion balloons are blow molded.

10. The drug delivery catheter of claim 2, further comprising perfusion means for allowing blood to flow through at least a portion of the catheter shaft.

11. The drug delivery catheter of claim 3, further comprising an additional lumen in the catheter shaft for perfusion.

12. The drug delivery catheter of claim 11, further comprising at least one opening in a wall of the catheter shaft, proximal the occlusion balloons, in fluid communication with the additional lumen.

13. The drug delivery catheter of claim 1, further comprising a dilatation balloon and a dilatation lumen in fluid communication with the dilatation balloon.

14. The drug delivery catheter of claim 3, further comprising a dilatation balloon and a dilatation lumen in fluid communication with the dilatation balloon, wherein the dilatation balloon is located between the occlusion balloons.

15. The drug delivery catheter of claim 1, wherein the guide wire lumen is proximate the periphery of the catheter shaft.

16. The drug delivery catheter of claim 12, wherein the additional lumen has a tapered distal end.

17. The drug delivery catheter of claim 2, further comprising at least one port through the catheter shaft to the guide wire lumen, to enable perfusion of blood through the guide wire lumen.

18. A catheter comprising:
   a catheter shaft having a distal portion, a distal end, and a proximal end;
   means for conveying a drug to an exterior of the catheter;
   means for delivering the drug from the proximal end to the means for conveying; and
   means for receiving a guide wire within the distal portion of the catheter shaft, the means for receiving including a means for the guide wire to exit the distal portion of the catheter shaft to the exterior of the catheter shaft.

19. The catheter of claim 18, wherein the means for conveying comprises at least one port in the distal portion of the catheter shaft, in fluid communication with the means for delivering.

20. The catheter of claim 18, wherein the means for conveying is a balloon attached to the distal portion of the catheter shaft, wherein the balloon defines a plurality of openings for enabling the drug to exit the balloon to the exterior of the catheter, the balloon being in fluid communication with the means for delivering.

21. The catheter of claim 20, wherein the balloon is adapted to dilatate a stenosis while conveying drugs.

22. The catheter of claim 21, wherein the balloon comprises an outer and an inner layer, the plurality of openings being in the outer layer, the outer and inner layer defining a region in fluid communication with the means for delivering, and the inner layer having an interior region, the catheter shaft further comprising a means for delivering inflation fluid to the interior region.

23. The catheter of claim 18, wherein the catheter shaft has a proximal end and the means for receiving the guide wire comprises a lumen within the distal portion of the catheter shaft, the lumen having a first end proximate the distal end of the catheter shaft and open to the exterior of the catheter, the lumen terminating at its proximal end substantially distal of the proximal end of the catheter shaft in a aperture open to the exterior of the catheter, the aperture being proximal to the means for conveying.

24. The catheter of claim 18, further comprising perfusion means.

25. The catheter of claim 18, further comprising occlusion means.

26. A dilatation-drug delivery catheter comprising:

a catheter shaft comprising a distal portion, a distal end and a proximal end;

a dilatation balloon attached to the distal portion of the catheter shaft;

a first occlusion balloon attached to the catheter shaft at a location distal to the dilatation balloon and a second occlusion balloon attached to the catheter shaft at a location proximal to the dilatation balloon;

the catheter shaft further comprising at least one drug delivery port in the distal portion of the catheter shaft, between the dilatation balloon and at least one of the occlusion balloons, at least one dilatation lumen in fluid communication with the dilatation balloon, at least one inflation lumen in fluid communication with the occlusion balloons, at least one drug delivery lumen fluidly communicating between the drug delivery port and the proximal end, and a guide wire lumen in the distal portion of the catheter shaft, the guide wire lumen having a first opening to an exterior of the catheter shaft at the distal end of the catheter shaft and a second opening to the exterior of the catheter shaft in the distal portion of the catheter shaft, proximal to the second occlusion balloon and substantially distal to the proximal end of the catheter shaft, such that a guide wire can enter the catheter shaft through the first opening and exit the catheter shaft through the second opening.

27. The catheter of claim 26, wherein the catheter shaft is integral.

28. The catheter of claim 26, wherein the catheter shaft comprises tubes which define the lumens.

29. A dilatation-drug delivery catheter comprising:

a catheter shaft comprising a distal portion, a distal end and a proximal end;

a dilatation balloon attached to the distal portion of the catheter shaft, the dilatation balloon having an outer and an inner layer wherein the inner layer defines an inner region proximate the catheter shaft and the outer and inner layers define an outer region, and the outer layer comprises a plurality of openings;

the catheter shaft further comprising a first lumen fluidly communicating between the outer region and the proximal end, and a second lumen in fluid communication with the inner region, and a third lumen in the distal portion of the catheter shaft for receiving a guide wire, the third lumen having a first opening to an exterior of the catheter shaft at the distal end of the catheter shaft and a second opening to the exterior of the catheter shaft in the distal portion of the catheter shaft, proximal to the dilatation balloon and substantially distal to the proximal end of the catheter shaft, such that the guide wire can enter the catheter shaft through the first opening and can exit the catheter shaft through the second opening.

30. The catheter of claim 29, wherein the first lumen is adapted to deliver a drug and the second lumen is adapted to deliver inflation fluid.

31. A drug delivery catheter comprising:

a catheter shaft having a distal portion, a distal end and a proximal end;

a drug delivery balloon attached to the distal portion of the catheter shaft, the drug delivery balloon including a plurality of ports extending through the balloon;

the catheter shaft further comprising at least one delivery lumen fluidly communicating between the drug delivery balloon and the proximal end, and a lumen in the distal portion of the catheter shaft for receiving a guide wire, the lumen having a first opening to the exterior of the catheter shaft at the distal end of the catheter shaft and a second opening to the exterior of the catheter shaft in the distal portion of the catheter shaft, proximal to the drug delivery balloon and substantially distal to the proximal end of the catheter shaft, such that the guide wire can enter the catheter shaft through the first opening and exit the catheter shaft through the second opening.

32. The catheter of claim 31, further comprising a perfusion lumen.

33. The catheter of claim 32, wherein the perfusion lumen extends from the distal end of the catheter shaft to the proximal end of the catheter shaft.

34. The catheter of claim 32, wherein the perfusion lumen extends from the distal end of the catheter shaft to a terminus proximal to the drug delivery balloon, the catheter shaft further comprising at least one port proximate the terminus of the perfusion lumen and extending through the catheter shaft to the perfusion lumen, to enable blood to enter the perfusion lumen.

35. The catheter of claim 34, wherein the perfusion lumen has a tapered distal end.

* * * * *